United States Patent [19]

Buffum et al.

[11] Patent Number: 5,145,824
[45] Date of Patent: Sep. 8, 1992

[54] ETHYLENE OXIDE CATALYST

[75] Inventors: John E. Buffum; Ruth M. Kowaleski, both of Houston, Tex.; William H. Gerdes, Hudson, Ohio

[73] Assignee: Shell Oil Company, Houston, Tex.

[21] Appl. No.: 804,494

[22] Filed: Dec. 9, 1991

Related U.S. Application Data

[63] Continuation of Ser. No. 643,606, Jan. 2, 1991, abandoned.

[51] Int. Cl.$^5$ ............... B01J 21/04; B01J 23/04; B01J 23/36; B01J 23/50
[52] U.S. Cl. .................. 502/216; 502/242; 502/243; 502/347; 502/348; 549/536
[58] Field of Search ............... 502/216, 242, 243, 347, 502/348

[56] References Cited

U.S. PATENT DOCUMENTS

| | | | |
|---|---|---|---|
| 4,428,863 | 1/1984 | Fry | 502/8 |
| 4,728,634 | 3/1988 | Buffum et al. | 502/243 |
| 4,761,394 | 8/1988 | Lauritzen | 502/348 |
| 4,766,105 | 8/1988 | Lauritzen | 502/216 |
| 4,812,437 | 3/1989 | Nojiri et al. | 502/348 X |
| 4,820,675 | 4/1989 | Lauritzen | 502/216 |
| 4,874,739 | 10/1989 | Boxhoorn | 502/218 |

FOREIGN PATENT DOCUMENTS

| | | | |
|---|---|---|---|
| 0247414 | 5/1987 | European Pat. Off. | |
| 266852 | 5/1988 | European Pat. Off. | 502/348 |

*Primary Examiner*—W. J. Shine

[57] ABSTRACT

The invention relates to ethylene oxide catalysts containing silver, alkali metal promoters, rhenium promoters and optionally rhenium co-promoters selected from sulfur, molybdenum, tungsten, chromium and mixtures thereof supported on a carrier consisting of at least 85 percent by weight of alpha alumina, from about 0.01 to about 6 percent by weight (measured as the oxide) of an added alkaline earth metal in the form of an oxide, from about 0.01 to about 5 percent by weight (measured as the dioxide) of added silicon in the form of an oxide and from zero to about 10 percent by weight (measured as the dioxide) of added zirconium in the form of an oxide. The invention also relates to an ethylene oxide process using the above catalyst.

33 Claims, No Drawings

ETHYLENE OXIDE CATALYST

This is a continuation of application Ser. No. 07/643,606, filed Jan. 2 1991, now abandoned.

FIELD OF THE INVENTION

The invention relates to silver-containing catalysts suitable for the preparation of ethylene oxide and to the use of the catalysts for the preparation of ethylene oxide. The catalysts are prepared using a unique alpha alumina carrier.

BACKGROUND OF THE INVENTION

Catalysts for the production of ethylene oxide from ethylene and molecular oxygen generally comprise silver supported on a carrier formed substantially of alpha alumina. Such catalysts are typically promoted with alkali metals. Other co-promoters, such as rhenium, or rhenium along with sulfur, molybdenum, tungsten and chromium can also be utilized. See, for example, U.S. Pat. No. 4,766,105, issued Aug. 23, 1988. While much research has been focused on promoters, more recently, work has been focused on the alumina supports and ways to modify them to produce improved catalysts.

European Patent Application 247,414, published Dec. 2, 1987, discloses the addition of silica to an alpha alumina carrier. U.S. Pat. No. 4,428,863, issued Jan. 31, 1984, discloses the addition of barium aluminate or barium silicate to alumina carriers during their manufacture. In U.S. Pat. No. 4,728,634, issued Mar. 1, 1988, silicon dioxide and an alkali metal salt are mixed with water and an aluminum compound and calcined to produce a silica- and alkali metal-containing alpha alumina support. In U.S. Pat. No. 4,874,739, Oct. 17, 1989, a tin compound and an alkali metal compound is incorporated into an alpha alumina carrier.

SUMMARY OF THE INVENTION

The invention relates to ethylene oxide catalysts comprising silver, alkali metal promoters, rhenium promoters and optionally rhenium co-promoters selected from sulfur, molybdenum, tungsten, chromium and mixtures thereof supported on a carrier comprising at least 85, preferably at least 90 and more preferably at least 95 percent by weight of alpha alumina, from about 0.01 to about 6 percent by weight (measured as the oxide) of an added alkaline earth metal in the form of an oxide, from about 0.01 to about 5 percent by weight (measured as the dioxide) of added silicon in the form of an oxide and from zero to about 10, preferably from about 0.1 to about 10 percent by weight (measured as the dioxide) of added zirconium in the form of an oxide. Preferably the alkaline earth metal is calcium and/or magnesium.

The carrier is prepared by mixing a powdered alpha alumina having a purity of greater than about 98 percent, an average particle size ranging from about 0.5 to about 5 microns and an average crystallite size ranging from about 0.1 to about 5 microns, an alkaline earth metal compound, a silicon compound and an optional zirconium compound, water, binder and/or burnout material to prepare a mixture which is extruded and calcined at a temperature ranging from about 1350° C. to about 1500° C.

DESCRIPTION OF THE PREFERRED EMBODIMENTS

The catalysts of the instant invention comprise a catalytically effective amount of silver, a promoting amount of alkali metal, a promoting amount of rhenium and optionally a promoting amount of a co-promoter selected from sulfur, chromium, molybdenum, tungsten and mixtures thereof, supported on a novel alpha alumina support. Descriptions of the carrier, the catalyst prepared with the carrier and the use of the catalyst are provided in detail below.

THE CARRIER

The novel carrier used to prepare the catalysts of the instant invention may, in general terms, be prepared from high purity alpha alumina powder, an alkaline earth metal oxide-providing compound, a silicon oxide-providing compound, an optional zirconium oxide-providing compound and conventional binders/burn-out agents.

The alpha alumina used in the carrier preparation generally has a purity greater than about 98%, preferably greater than about 98.5% and less than about 0.06% by weight, such as from 0.02 to 0.06% by weight, of soda impurities. The alumina has the form of a fine powder, preferably one having an average particle size of from about 0.5 to about 100 microns. Smaller sizes such as from about 0.5 to about 5 microns and more preferably from about 1 to about 4 microns are particularly suitable. The average size may be determined by measuring the maximum dimension of a number of particles and taking the average thereof. The average crystallite size, which can be from about 0.1 to about 5 microns and more preferably from about about 2 to about 4 microns, is determined by measuring the maximum dimension of a number of crystallites and taking the average thereof. The alpha alumina will be present in the calcined carrier in an amount greater than about 85%, preferably 90%, and more preferably 95% by weight of the total carrier.

The alkaline earth metal component of the carrier can be present in an amount that represents from about 0.01 to about 6% by weight (measured as the oxide, MO) of the carrier weight but preferably the amount present is from about 0.03 to about 5.0%, more preferably from about 0.05 to about 4% and especially from about 0.05 to about 2.0% by weight.

The alkaline earth metal compounds that may be used to prepare the carriers are oxides or compounds which are decomposable to or which form oxides upon calcination. Examples include carbonates, nitrates and carboxylates. Suitable compounds include the alkaline earth oxides themselves, as well as the mixed oxides such as the alkaline earth metal silicates, aluminates, aluminosilicates, zirconates and the like. The preferred compounds are calcium nitrate, calcium oxide and calcium silicate ($CaSiO_3$).

The silicon compounds used to prepare the carriers are oxides or compounds which are decomposable to or which form oxides upon calcination. Suitable compounds include silicon dioxide itself, as well as the mixed oxides such as the alkaline earth metal silicates, zirconium silicates, aluminosilicates including zeolites, hydrolyzable silicon compounds, polysiloxanes and the like. The amount of silicon component used should be such as to provide, in the final carrier composition, from about 0.01 to about 5.0%, preferably from about 0.03 to about 4.0% and most conveniently from about 0.05 to about 3.0% by weight (measured as silica).

The zirconium component, while optional, is preferably present in an amount that is from about 0.1 to about 10.0%, preferably from about 0.3 to about 5.0% and especially from about 0.5 to about 2.0% by weight based on the carrier weight. Where zirconia is generated in situ, the amount used should be selected to give a final proportion within these parameters.

The zirconium compounds which may be used to prepare the carriers are oxides or compounds which are decomposable to or which form oxides upon calcination. Examples include carbonates, nitrates and carboxylates. Suitable compounds include zirconium nitrate, zirconium dioxide, as well as the mixed oxides such as zirconium silicates, zirconium aluminosilicates, zirconates and the like. The preferred compound is zirconium dioxide.

Preferred carrier compositions comprise the alkaline earth metal- and the silicon-containing compounds in the form of a single compound, an alkaline earth metal silicate, which may be added as an original component or generated in situ by the reaction of silica or silica generating compounds with compounds that decompose to the alkaline earth metal oxide upon heating, with the amount of the oxide formed being in stoichiometric equivalent to or excess over the silica.

While the alkaline earth metal component of the catalyst can be chosen from magnesium, calcium, strontium and barium, the preferred embodiments are calcium and magnesium, mixtures thereof with calcium the most preferred. In the further description of this invention reference will frequently be made to the calcium form for the sake of simplicity.

The preferred carriers may be prepared by mixing a powdered alpha alumina, calcium silicate and zirconia with water and a binder and/or burnout material to prepare a mixture which is then extruded and calcined at a temperature ranging from about 1350° C. to about 1500° C.

The alpha alumina powder is most preferably combined with calcium silicate itself but, as indicated above, it is also possible to use a calcium oxide-generating compound and silica or a silica-generating compound in such proportions that on heating calcium silicate is produced. These components are mixed with zirconia or a zirconia-generating compound, (where present), a burnout/binding agent and water, formed into shapes and calcined.

The burnout agent is a material that is added to the mixture such that upon calcination, it is completely removed from the carrier, leaving a controlled porosity in the carrier. These materials are carbonaceous materials such as coke, carbon powders, graphite, powdered plastics such as polyethylene, polystyrene and polycarbonate, rosin, cellulose and cellulose based materials, sawdust and other plant materials such as ground nut shells, e.g. pecan, cashew, walnut and filbert shells. Carbon-based burnout agents can also serve as binding agents. The burnout agents are provided in an amount and size distribution to provide a final carrier having a water pore volume ranging from about 0.2 to about 0.6, preferably 0.3 to 0.5 cc/g. Preferred burnout agents are cellulose-derived materials, such as ground nut shells.

The term "binding agent" as used herein refers to an agent that holds together that various components of the carrier prior to calcination to form an extrudable paste, i.e., the so-called low temperature binding agent. The binding agent also facilitates the extrusion process by adding lubricity. Typical binding agents include alumina gels, particularly in combination with a peptizing agent such as nitric or acetic acid. Also suitable are the carbon based materials that can also serve as burnout agents, such as the celluloses and substituted celluloses such as methylcellulose, ethylcellulose and carboxyethylcellulose, stearates such as organic stearate esters, e.g. methyl or ethyl stearate, waxes, polyolefin oxides and the like. Preferred binding agents are polyolefin oxides.

The use of calcium silicate, whether prepared directly or in situ with the constraints described above, allows the use of bonds containing, overall, a lower amount of silica than is present in conventional bonds. It also permits the avoidance of an excess of silicon dioxide which typically contains deleterious amounts of sodium, iron and/or potassium impurities, especially when present in clays, bentonite and the like.

The role of the zirconia, where used, is not fully understood but it appears to stabilize certain partial oxidation catalyst recipes. Calcium silicate also appears to stabilize at least a proportion of the zirconia in the more active tetragonal form instead of the monoclinic form to which the mixed phase reverts when heated in the absence of calcium silicate.

When reference is made to oxide(s) of alkaline earth metal(s), silicon or zirconium which are present in the finished carrier and/or catalyst, it is understood that the oxide may be an oxide of only one metal or may be a complex oxide made up of the indicated metal and one or more of the other metals as well as alumina and/or catalyst promoters, such as, alkali metals.

After the components of the carrier are mixed together, say by mulling, the mixed material is extruded into shaped pellets, for example, cylinders, rings, trilobes, tetralobes and the like. The extruded material is dried to remove water that could convert to stream during calcination and destroy the extrudate shapes. After drying to a low water content, say less than about 2%, the extruded material is calcined under conditions sufficient to remove burnout agents and binding agents and to fuse the alpha alumina particles into a porous, hard mass. Calcination is typically carried out in an oxidizing atmosphere, say oxygen gas or preferably air and at a maximum temperature greater than about 1300° C. and preferably ranging from about 1350° C. to about 1500° C. Times at these maximum temperatures typically range from about 0.1 to 10 hours, preferably from about 0.5 to 5 hours.

The calcined carriers and catalysts made therefrom will typically have pore volumes (water) ranging from about 0.2 to about 0.6, preferably from about 0.3 to about 0.5 cc/g and surface areas ranging from about 0.15 to about 3, preferably for about 0.3 to about 2 m$^2$/g.

The carrier formulation preferably has a low soda content which is less than abut 0.06% by weight. In practice it is very difficult to obtain a sodium-free formulation and soda contents from about 0.02 to 0.06% by weight are usually found acceptable.

The carriers described above are particularly suited for preparing ethylene oxide catalysts which have high initial selectivities.

THE CATALYST

The catalysts of the instant invention comprise a catalytically effective amount of silver, a promoting amount of alkali metal, a promoting amount of rhenium and optionally a promoting amount of a co-promoter selected from sulfur, chromium, molybdenum, tungsten and mixtures thereof, supported on a novel alpha alumina support. In a preferred embodiment the alkali metal promoter is a higher alkali metal of potassium, rubidium, cesium or mixtures thereof. In a particularly preferred embodiment the alkali metal is cesium. Cesium in combination with lithium also provides very desirable advantages and is a preferred combination. Other promoters may be present such as co-promoters selected from sulfur, molybdenum, tungsten, chromium and mixtures thereof. Sulfate is a particularly preferred co-promoter. These catalysts and their preparation are particularly described in U.S. Pat. No. 4,761,394, issued August 1988, U.S. Pat. No. 4,766,105, issued Aug. 23, 1988 and U.S. Pat. No. 4,820,675, issued Apr. 11, 1989, all of which are incorporated by reference herein.

The amount of silver present on the catalyst will typically range from about 1 to about 25, preferably from about 5 to about 20 percent by weight of the total catalyst. The amount of alkali metal promoter preferably present on the catalyst generally lies between abut 10 and about 3000, preferably between about 20 and about 2000 and more preferably between about 50 and about 1500 parts by weight (basis metal) per million parts by weight of total catalyst. The amount of rhenium promoter preferably present on the catalyst generally lies between about 0.1 to about 10, more preferably between about 0.2 to about 5 micromoles (basis metal) per gram of total catalyst. The rhenium co-promoter, when present, preferably will be present on the catalyst in an amount between 0 to about 15, preferably between about 0.1 to about 15 micromoles (basis metal) per gram of total catalyst.

Methods for preparing the instant catalysts are conventional and are described in the above referenced patents. In general, the carrier is mixed with an aqueous solution of a silver complex, preferably in the presence of a solubilizing agent such as ethylenediamine, so that the carrier is impregnated with this solution, after which the carrier is separated from the solution and subsequently dried. The impregnated carrier is then heated to a temperature of between about 100° C. and about 400° C. for a period necessary for the silver complex to decompose and form a finely distributed layer of metallic silver which adheres to the carrier surfaces. The promoters may also be dissolved in the silver-containing solution to provide the desired amounts or they may be applied separately or together to the carrier by an impregnation step separate from the silver impregnation step. Preferably, silver and promoters are all combined in one impregnation step.

THE PROCESS

In commercial operation, ethylene and oxygen are converted to ethylene oxide in an ethylene oxide reactor which comprises a large fixed tube sheet heat exchanger containing several thousand tubes filled with catalyst. A coolant is used on the shell side of the reactor to remove the heat of reaction. Coolant temperatures are frequently utilized as an indication of catalyst activity, high coolant temperatures corresponding to lower catalyst activities.

In the reaction of ethylene with oxygen to produce ethylene oxide, the ethylene is present in at least a double molecular quantity, but the quantity of ethylene employed is generally much higher. The conversion is therefore conveniently calculated according to the quantity of converted oxygen in the reaction and one speaks of oxygen conversion. This oxygen conversion is dependent on the temperature of the reaction and is a measure of the activity of the catalyst. For example, the value $T_{40}$ refers to the temperature at 40 mol % conversion of the oxygen fed to the reactor, T being the reactor temperature, or more preferably the coolant temperature, which latter is directly related to the former. The temperatures are generally higher for a higher conversion and are dependent on the catalyst employed and the reaction conditions. Selectivity is an indication of catalyst efficiency and indicates the mol % of ethylene in the feed which is converted to ethylene oxide in the product. The selectivity is indicated as, for example, $S_{40}$, which refers to the selectivity at 40% oxygen conversion.

The conditions for carrying out an ethylene oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydrocarbons, presence of moderating agents to control the catalytic action, for example, 1-2-dichloroethane, vinyl chloride, ethyl chloride or chlorinated polyphenyl compounds, the desirability of employing recycle operations or applying successive conversions in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective. For purposes of illustration only, the following table shows the range of conditions that are often used in current commercial ethylene oxide reactor units and which are also suitable for the instant process.

TABLE 1

| | |
|---|---|
| GHSV* | 1500–10,000 |
| Inlet pressure | 150–400 psig |
| Inlet Feed | |
| Ethylene | 1–40% |
| $O_2$ | 3–12% |
| $CO_2$ | 2–40% |
| Ethane | 0–3% |
| Argon and/or methane and/or nitrogen diluent chlorohydrocarbon moderator | 0.3–20 ppmv total |
| Coolant temperature | 180–315° C. |
| Catalyst temperature | 180–325° C. |
| $O_2$ conversion level | 10–60% |
| EO production (work rate) | 2–16 lbs. EO/cu. ft. catalyst/hr. |

*Liters of gas at standard temperature and pressure passing over the one liter of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200° C. to about 325° C.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

Illustrative Embodiments

Carrier Preparation

Carrier A

An alpha alumina powder (alumina #10) having the properties listed in Table 2 below was used to prepare the carrier.

TABLE 2

| Properties for Alumina #10 | |
|---|---|
| Median Particle Size | 3.0–3.4 microns |
| Average Crystallite Size | 1.8–2.2 microns |
| Soda Content | 0.02–0.06% by wt. |

This powder was used to prepare a formulation of the following ceramic components:
Alpha Alumina: 98.8%
Zirconia: 1.0%
Calcium Silicate: 0.2%

Based on the weight of this formulation, the following were added in the indicated proportions:
Burn-out (walnut shell flour): 25.0%
Boric Acid: 0.1%
Extrusion Aid (polyolefin oxide): 5.0%

After the above had been mixed for 45 seconds, enough water was added to give an extrudable mixture, (about 30% in practice), and mixing was continued for a further 4 minutes. At this point 5% (based on the weight of the ceramic components), of vaseline was added and mixing was continued for a further 3 minutes.

This material was extruded in the form of 5/16 in. ×5/16 in. hollow cylinders and dried to less than 2% moisture. These were then fired in a tunnel kiln to a maximum temperature of 1390° C. for about 4 hours.

After processing in this manner the carrier had the following properties:

| Water Absorption | 40.8% |
|---|---|
| Crush Strength | 18.7 lbs |
| Surface Area | 0.54 m²/g |
| Total Pore Volume (Hg) | 0.43 cc/g |
| Median Pore Diameter | 4.6 microns |
| Leachable Components (in 10% nitric acid) in ppm: | |
| Na | 141 |

| -continued | |
|---|---|
| K | 55 |
| Ca | 802 |
| Al | 573 |
| SiO$_2$ | 1600 |

Additional carriers were prepared in a manner similar to the method described above with the exception that different starting materials were used. The properties of the different starting aluminas are shown in Table 3 below.

TABLE 3

| Properties for Aluminas Nos. 11 and 49 | | |
|---|---|---|
| | #11 | #49 |
| Median Particle Size | 3.0–3.6 microns | 3.0–4.0 microns |
| Average Crystallite Size | 1.6–1.8 microns | 1.0–1.4 microns |
| Soda Content | 0.02–0.06% wt. | 0.02–0.06% wt. |

The water pore volumes, surface areas and firing temperatures are shown in Table 4 and the other starting materials and their amounts are shown in Table 5 below.

A comparative carrier was made with alumina #10 in the manner described above for carrier A except that no zirconia or calcium silicate were added. This comparative carrier is denoted as Comp-A. Its properties are provided in Table 4 below.

TABLE 4

| Carrier | Water P.V., cc/g | SA, m²/g | Firing Temp, °C. |
|---|---|---|---|
| Comp-A | 0.46 | 0.52 | 1371 |
| A | 0.41 | 0.54 | 1390 |
| B | 0.42 | 0.52 | 1371 |
| C | 0.39 | 0.49 | 1371 |
| D | 0.34 | 0.60 | 1371 |
| E | 0.26 | 0.16 | 1371 |
| F | 0.30 | 0.34 | 1371 |
| G | 0.27 | 0.25 | 1371 |
| H | 0.35 | 0.57 | 1454 |
| I | 0.43 | 0.60 | 1400 |
| J | 0.44 | 0.51 | 1393 |
| K | 0.37 | 0.50 | 1371 |
| L | 0.42 | 0.59 | 1371 |
| M | 0.38 | 0.51 | 1371 |
| N | 0.44 | 0.73 | 1371 |
| O | 0.42 | 0.74 | 1371 |
| P | 0.50 | 0.66 | 1413 |
| Q | 0.47 | 0.68 | 1413 |
| R | 0.51 | 0.81 | 1413 |
| S | 0.43 | 0.45 | 1413 |
| T | 0.43 | 0.38 | 1413 |
| U | 0.54 | 1.09 | 1413 |
| V | 0.55 | 0.66 | 1413 |
| W | 0.54 | 0.98 | 1413 |
| X | 0.42 | 0.41 | 1400 |
| Y | 0.47 | 0.60 | 1400 |
| Z | 0.41 | 0.44 | 1371 |
| AA | 0.40 | 0.46 | 1371 |

TABLE 5

| Carrier | Alumina | Compound A* | Compound B* | Compound C* |
|---|---|---|---|---|
| Comp-A | #10 | 0 | 0 | 0 |
| A | #10 | ZrO$_2$ (1.0) | CaSiO$_3$ (0.20) | |
| B | #10 | ZrO$_2$ (1.0) | CaSiO$_3$ (0.10) | |
| C | #10 | ZrO$_2$ (1.0) | CaSiO$_3$ (0.40) | |
| D | #10 | | CaSiO$_3$ (0.40) | |
| E | #10 | | CaSiO$_3$ (0.20) | |
| F | #10 | ZrO$_2$ (1.0) | CaSiO$_3$ (2.00) | |
| G | #10 | ZrO$_2$ (1.0) | CaSiO$_3$ (4.00) | |
| H | #10 | ZrO$_2$ (1.0) | CaAl$_2$SiO$_6$ (0.20) | |
| I | #10 | ZrO$_2$ (1.0) | Ca(NO$_3$)$_2$ (0.28) | SiO$_2$ (0.10) |
| J | #10 | ZrO$_2$ (0.8) | Ba(NO$_3$)$_2$ (0.47) | ZrSiO$_4$ (0.31) |

TABLE 5-continued

| Carrier | Alumina | Compound A* | Compound B* | Compound C* |
|---|---|---|---|---|
| K | #10 | $ZrO_2$ (1.0) | $CaSiO_3$ (0.20) | $Ca(NO_3)_2$ (0.29) |
| L | #10 | $ZrO_2$ (1.0) | $MgSiO_3$ (0.20) | |
| M | #10 | $ZrO_2$ (1.0) | $MgSiO_3$ (2.20) | |
| N | #10 | $ZrO_2$ (1.0) | $Mg_3Al_2(SiO_4)_3$ (0.20) | |
| O | #10 | $ZrO_2$ (1.0) | $SrSiO_3$ (2.20) | |
| P | #49 | $ZrO_2$ (1.0) | $CaSiO_3$ (0.30) | |
| Q | #49 | $ZrO_2$ (1.0) | $CaSiO_3$ (0.30) | $Ca(NO_3)_2$ (0.29) |
| R | #49 | $ZrSiO_4$ (0.46) | $Ca(NO_3)_2$ (0.44) | |
| S | #49 | $ZrSiO_4$ (0.46) | $Ca(NO_3)_2$ (0.73) | |
| T | #49 | $ZrSiO_4$ (0.46) | $Ca(NO_3)_2$ (1.02) | |
| U | #49 | $ZrSiO_4$ (0.46) | $Ba(NO_3)_2$ (0.70) | |
| V | #49 | $ZrSiO_4$ (0.46) | $Ba(NO_3)_2$ (1.17) | |
| W | #49 | $ZrSiO_4$ (0.46) | $Ba(NO_3)_2$ (1.63) | |
| X | #11 | $ZrO_2$ (1.0) | mullite (0.07) | $Ca(NO_3)_2$ (0.22) |
| Y | #11 | $ZrO_2$ (1.0) | mullite (0.07) | $Ba(NO_3)_2$ (0.13) |
| Z | #10 | $ZrO_2$ (5.0) | $CaSiO_3$ (0.20) | |
| AA | #10 | $ZrO_2$ (10.0) | $CaSiO_3$ (0.20) | |

*Weight percent basis alumina.

Catalyst Preparation

Carrier A described above is a preferred carrier and was used to prepare an ethylene oxide catalyst. Into a solution of water and ethylenediamine were dissolved silver oxalate, cesium hydroxide, ammonium perrhenate, lithium sulfate and lithium nitrate in amounts sufficient to provide in the impregnated carrier (basis dry weight of carrier) 13.5% wt silver, 437 ppm cesium, 1.5 micromoles/g of ammonium perrhenate, 1.5 micromoles/g of lithium sulfate and 12 micromoles/g of lithium nitrate. Approximately 30 g of the carrier was placed under 25 mm vacuum for 3 minutes at room temperature. Approximately 50 g of the impregnating solution was then introduced to submerge the carrier, and the vacuum was maintained at 25 mm for an additional 3 minutes. At the end of this time, the vacuum was released, and the excess impregnating solution was removed from the carrier by centrifugation for 2 minutes at 500 rpm. The impregnated carrier was then cured by being continuously shaken in a 300 cu. ft./hr. air stream at 250° C. for 5 minutes. The cured catalyst, denoted as C-A[1], is ready for testing.

The actual silver content of the catalyst can be determined by any of a number of standard, published procedures. The actual level of rhenium on the catalysts prepared by the above process can be determined by extraction with 20 mM aqueous sodium hydroxide solution, followed by spectrophotometric determination of the rhenium in the extract. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as the other alkali metals, is measured by extraction from the catalyst by boiling 10 grams of whole catalyst in 25 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

The carrier listed in Tables 4 and 5 were used to prepare the catalysts listed in Table 6. C-A and C-A[1] refer to catalysts prepared with carrier A, C-B refer to catalysts prepared with carrier B, etc. C-Comp-A is the catalyst made from carrier Comp-A.

TABLE 6

| Catalyst | Ag wt % | Cs ppm | $NH_4ReO_4$ umol/g | $Li_2SO_4$ umol/g | $LiNO_3$ umol/g |
|---|---|---|---|---|---|
| C-Comp-A | 13.2 | 501 | 1.5 | 1.5 | 4 |
| C-A | 13.5 | 463 | 1.5 | 1.5 | 4 |
| C-A[1] | 13.5 | 437 | 1.5 | 1.5 | 12 |
| C-B | 13.2 | 506 | 1.5 | 1.5 | 4 |
| C-C | 13.2 | 480 | 1.5 | 1.5 | 4 |
| C-D | 13.2 | 470 | 1.5 | 1.5 | 4 |
| C-E | 10.0 | 274 | 0.75 | 0.75 | 4 |
| C-F | 12.0 | 277 | 1.0 | 1.0 | 4 |
| C-G | 12.0 | 306 | 1.0 | 1.0 | 4 |
| C-H | 13.4 | 589 | 1.5 | 1.5 | 4 |
| C-I | 13.2 | 665 | 2.0 | 2.0 | 4 |
| C-J | 14.5 | 468 | 1.5 | 1.5 | 4 |
| C-K | 13.2 | 442 | 1.5 | 1.5 | 4 |
| C-L | 13.2 | 540 | 1.5 | 1.5 | 4 |
| C-L[1] | 13.2 | 481 | 1.5 | 0 | 4 |
| C-M | 13.2 | 415 | 1.5 | 1.5 | 4 |
| C-M[1] | 13.2 | 382 | 1.5 | 0 | 4 |
| C-N | 14.5 | 620 | 1.5 | 1.5 | 4 |
| C-N[1] | 14.5 | 573 | 1.5 | 0 | 4 |
| C-O | 14.5 | 547 | 1.5 | 1.5 | 4 |
| C-P | 14.5 | 599 | 2.0 | 2.0 | 4 |
| C-Q | 14.5 | 572 | 1.5 | 1.5 | 4 |
| C-R | 14.5 | 795 | 2.0 | 2.0 | 4 |
| C-S | 13.2 | 510 | 1.5 | 1.5 | 4 |
| C-T | 13.2 | 520 | 1.5 | 1.5 | 4 |
| C-U | 14.5 | 887 | 2.0 | 2.0 | 4 |
| C-V | 14.5 | 750 | 2.0 | 2.0 | 4 |
| C-W | 14.5 | 786 | 2.0 | 2.0 | 4 |
| C-X | 13.3 | 500 | 1.5 | 1.5 | 4 |
| C-Y | 14.5 | 620 | 1.5 | 1.5 | 4 |

THE PROCESS

The following describes the standard microreactor catalyst test conditions and procedures used to test the catalysts for the production of ethylene oxide from ethylene and oxygen.

Three to five grams of crushed catalyst (14–20 mesh) are loaded into a 0.23 inch internal diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 3300 cc of gas per cc of catalyst per hour. The inlet gas pressure is 210 psig.

The gas mixture passed through the catalyst bed (in once-through operation) during the entire test run (including startup) consists of 30% ethylene, 8.5% oxygen, 5 to 7% carbon dioxide, 0.5% argon, balance nitrogen, and 0.5 to 5 ppmv ethyl chloride.

Prior to being contacted with the reactant gases, the catalysts are typically pretreated with nitrogen gas at 225° C. for 3 hours for all fresh catalysts and for 24 hours or longer for aged, but untested catalysts.

The initial reactor (heat medium) temperature is 225° C. After 1 hour at this initial temperature, the temperature is increased to 235° C. for 1 hour, followed by 245° C. for 1 hour. The temperature is then adjusted so as to achieve a constant oxygen conversion level of 40% ($T_{40}$). The moderator level is varied and run for 4–24 hours at each level to determine the optimum moderator level for maximum selectivity. Performance data at the optimum moderator level and at $T_{40}$ are usually obtained when the catalyst has been onstream for a total of about 24 hours and are provided in the examples given below. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performances of catalysts tested at different times, all catalysts described in this illustrative embodiment were tested simultaneously with a standard reference catalyst. All performance data reported in this illustrative embodiment are corrected to conform to the average initial performance of the reference catalyst which was $S_{40}=81.0\%$ and $T_{40}=230°$ C.

The catalysts prepared above were tested using the above procedure and the results are given in the table below.

TABLE 7

| Catalyst | $S_{40}$, % | $T_{40}$, °C. |
|---|---|---|
| C-Comp-A | 85.1 | 261 |
| C-A | 85.8 | 258 |
| C-A[1] | 86.0 | 258 |
| C-B | 86.3 | 261 |
| C-C | 86.0 | 255 |
| C-D | 86.5 | 259 |
| C-E | 83.8 | 266 |
| C-F | 85.6 | 259 |
| C-G | 85.0 | 276 |
| C-H | 85.9 | 267 |
| C-I | 85.2 | 263 |
| C-J | 84.2 | 262 |
| C-K | 87.0 | 258 |
| C-L | 87.1 | 250 |
| C-L[1] | 87.3 | 252 |
| C-M | 86.8 | 260 |
| C-M[1] | 86.0 | 252 |
| C-N | 87.0 | 257 |
| C-N[1] | 85.2 | 257 |
| C-O | 87.1 | 265 |
| C-P | 84.3 | 247 |
| C-Q | 85.5 | 252 |
| C-R | 86.6 | 260 |
| C-S | 83.8 | 250 |
| C-T | 85.7 | 264 |
| C-U | 82.9 | 254 |
| C-V | 83.5 | 260 |
| C-W | 81.9 | 252 |
| C-X | 85.6 | 254 |
| C-Y | 85.3 | 258 |

We claim:

1. An ethylene oxide catalyst for the vapor phase production of ethylene oxide from ethylene and oxygen comprising a catalytically effective amount of silver, a promoting amount of alkali metal and a promoting amount of rhenium supported on a carrier comprising at least 85 percent by weight of alpha alumina, from about 0.05 to about 4 percent by weight (measured as the oxide, MO) of an alkaline earth metal in the form of an oxide, from about 0.01 to about 5 percent by weight (measured as the dioxide) of silicon in the form of an oxide and from zero to about 10 percent by weight (measured as the dioxide) of zirconium in the form of an oxide.

2. The catalyst of claim 1 wherein the carrier has a water pore volume between about 0.2 and about 0.6 cc/g and a surface area between about 0.15 and about 3 m²/g.

3. The catalyst of claim 2 wherein the carrier has a water pore volume between about 0.3 and about 0.5 cc/g and a surface area between about 0.3 and about 2 m²/g.

4. The catalyst of claim 1 wherein, in the carrier, the alpha alumina is present in an amount at least 90 weight percent, the silicon oxide ranges from about 0.03 to about 4 weight percent and the zirconium oxide ranges from about 0.3 to about 5 weight percent.

5. The catalyst of claim 4 wherein, in the carrier, the alpha alumina is present in an amount at least 95 weight percent, the silicon oxide ranges from about 0.05 to about 3 weight percent and the zirconium oxide ranges from about 0.5 to about 2 weight percent.

6. The catalyst of claim 5 wherein, in the carrier, the alkaline earth metal oxide is selected from the group consisting of calcium oxide, magnesium oxide and mixtures thereof and is present in an amount ranging from about 0.05 to about 2% by weight.

7. The catalyst of claim 1 wherein the alpha alumina has a soda content of less than about 0.06% weight.

8. The catalyst of claim 1 wherein the catalyst additionally comprises a rhenium co-promoter selected from the group consisting of sulfur, molybdenum, tungsten, chromium and mixtures thereof supported on the carrier.

9. The catalyst of claim 1 wherein the silver ranges from about 1 to about 25 percent by weight of the total catalyst, the alkali metal ranges from about 10 to about 3000 parts per million by weight of the total catalyst and the rhenium ranges from about 0.1 to about 10 micromoles per gram of catalyst.

10. The catalyst of claim 9 wherein the catalyst additionally comprises a rhenium co-promoter selected from the group consisting of sulfur, molybdenum, tungsten, chromium and mixtures thereof supported on the carrier in an amount ranging from about 0.1 to about 15 micromoles per gram of catalyst.

11. An ethylene oxide catalyst for the vapor phase production of ethylene oxide from ethylene and oxygen comprising a catalytically effective amount of silver, a promoting amount alkali metal and a promoting amount of rhenium supported on a carrier prepared by a process which comprises:

(a) mixing:
(i) an alpha alumina powder having a purity of greater than about 98 percent, an average crystallite size between about 0.1 and about 5 microns, (ii) an alkaline earth metal oxide or compound which is decomposable to or forms an oxide upon calcination, (iii) a silicon oxide or compound which is decomposable to or forms an oxide upon calcination and (iv) an optional zirconium oxide or compound which is decomposable to or forms an oxide upon calcination; with water and a binder/burnout agent in amounts sufficient to provide in the finished carrier alpha alumina in an amount at least 85 percent by weight, alkaline earth metal oxide in an amount ranging from about 0.01 to about 6 percent by weight, silicon oxide in an amount ranging from about 0.01 to about 5 percent by weight and zirconium oxide in an amount ranging from zero to about 10 percent by weight, (b) extruding the resulting mixture of step (a) to form pellets and (c) calcining the pellets at a temperature greater than 1300° C. for a time sufficient to produce a carrier having a surface area ranging from about 0.15 to about 3 square meters per gram and a water pore volume ranging from about 0.2 to about 0.6 cubic centimeters per gram;

12. The catalyst of claim 11 wherein, in the carrier, the alpha alumina powder has a purity of greater than about 98.5 percent, an average crystallite size between about 2 and about 4 microns and a soda content of less than about 0.06% weight; and components are provided in amounts sufficient to provide in the finished carrier alpha alumina in an amount at least 90 percent by weight, alkaline earth metal oxide in an amount ranging from about 0.03 to about 5 percent by weight, silicon oxide in an amount ranging from about 0.03 to about 4 percent by weight and zirconium oxide in an amount ranging from 0.3 to about 5 percent by weight.

13. The catalyst of claim 12 wherein, in the carrier, components are provided in amounts sufficient to provide in the finished carrier alpha alumina in an amount at least 95 percent by weight, alkaline earth metal oxide in an amount ranging from about 0.05 to about 4 percent by weight, silicon oxide in an amount ranging from about 0.05 to about 3 percent by weight and zirconium oxide in an amount ranging from 0.5 to about 2 percent by weight.

14. The catalyst of claim 13 wherein, in the carrier, the alkaline earth metal oxide or compound is selected from the group consisting of calcium oxide or compound, magnesium oxide or compound and mixtures thereof and is present in an amount sufficient to provide in the finished carrier alkaline earth metal oxide in an amount ranging from about 0.05 to about 2% by weight.

15. The catalyst of claim 11 wherein, in the carrier, the pellets are calcined at a temperature between about 1350° C. to about 1500° C. for a time sufficient to produce a carrier having a surface area ranging from about 0.3 to about 2 square meters per gram and a water pore volume ranging from about 0.3 to about 0.5 cubic centimeters per gram;

16. The catalyst of claim 11 wherein the catalyst additionally comprises a rhenium co-promoter selected from the group consisting of sulfur, molybdenum, tungsten, chromium and mixtures thereof supported on the carrier.

17. The catalyst of claim 11 wherein the silver ranges from about 1 to about 25 percent by weight of the total catalyst, the alkali metal ranges from about 10 to about 3000 parts per million by weight of the total catalyst and the rhenium ranges from about 0.1 to abut 10 micromoles per gram of catalyst.

18. The catalyst of claim 17 wherein the catalyst additionally comprises a rhenium co-promoter selected from the group consisting of sulfur, molybdenum, tungsten, chromium and mixtures thereof supported on the carrier in an amount ranging from about 0.1 to about 15 micromoles per gram of catalyst.

19. An ethylene oxide catalyst for the vapor phase production of ethylene oxide from ethylene and oxygen comprising a catalytically effective amount of silver, a promoting amount of alkali metal and a promoting amount of rhenium supported on a carrier comprising at least 85 percent by weight of alpha alumina, from about 0.01 to about 6 percent by weight (measured as the oxide, MO) of an alkaline earth metal in the form of an oxide, from about 0.01 to about 5 percent by weight (measured as the dioxide) of silicon in the form of an oxide and from 0.3 to about 5 percent by weight (measured as the dioxide) of zirconium in the form of an oxide.

20. The catalyst of claim 19 wherein the carrier has a water pore volume between about 0.2 and about 0.6 cc/g and a surface area between about 0.15 and about 3 $m^2/g$.

21. The catalyst of claim 20 wherein the carrier has a water pore volume between about 0.3 and about 0.5 cc/g and a surface area between about 0.3 and about 2 $m^2/g$.

22. The catalyst of claim 19 wherein, in the carrier, the alpha alumina is present in an amount at least 90 weight percent, the alkaline earth metal oxide ranges from about 0.03 to about 5 weight percent and the silicon oxide ranges from about 0.03 to about 4 weight percent.

23. The catalyst of claim 22 wherein, in the carrier, the alpha alumina is present in an amount at least 95 weight percent, the alkaline earth metal oxide ranges from about 0.05 to about 4 weight percent, the silicon oxide ranges from about 0.05 to about 3 weight percent and the zirconium oxide ranges from about 0.5 to about 2 weight percent.

24. The catalyst of claim 23 wherein, in the carrier, the alkaline earth metal oxide is selected from the group consisting of calcium oxide, magnesium oxide and mixtures thereof and is present in an amount ranging from about 0.05 to about 2% by weight.

25. The catalyst of claim 19 wherein the alpha alumina has a soda content of less than about 0.06% weight.

26. The catalyst of claim 19 wherein the catalyst additionally comprises a rhenium co-promoter selected from the group consisting of sulfur, molybdenum, tungsten, chromium and mixtures thereof supported on the carrier.

27. The catalyst of claim 19 wherein the silver ranges from about 1 to about 25 percent by weight of the total catalyst, the alkali metal ranges from about 10 to about 3000 parts per million by weight of the total catalyst and the rhenium ranges from about 0.1 to about 10 micromoles per gram of catalyst.

28. The catalyst of claim 27 wherein the catalyst additionally comprises a rhenium co-promoter selected from the group consisting of sulfur, molybdenum, tungsten, chromium and mixtures thereof supported on the carrier in an amount ranging from about 0.1 to about 15 micromoles per gram of catalyst.

29. The catalyst of claim 1 wherein, in the carrier, the alkaline earth metal oxide is selected from the group consisting of calcium oxide, magnesium oxide and mixtures thereof.

30. The catalyst of claim 2 wherein, in the carrier, the alkaline earth metal oxide is selected from the group consisting of calcium oxide, magnesium oxide and mixtures thereof.

31. The catalyst of claim 3 wherein, in the carrier, the alkaline earth metal oxide is selected from the group consisting of calcium oxide, magnesium oxide and mixtures thereof.

32. The catalyst of claim 11 wherein, in the carrier, the alkaline earth metal oxide or compound is selected from the group consisting of calcium oxide or compound, magnesium oxide or compound and mixtures thereof.

33. The catalyst of claim 12 wherein, in the carrier, the alkaline earth metal oxide or compound is selected from the group consisting of calcium oxide or compound, magnesium oxide or compound and mixtures thereof.

* * * * *